United States Patent [19]
Roh

[11] Patent Number: 5,138,794
[45] Date of Patent: Aug. 18, 1992

[54] METHOD FOR PRODUCING LILIUM ELEGANS

[75] Inventor: Mark S. Roh, Beltsville, Md.

[73] Assignee: The United States of America as represented by the Secretary of Agriculture, Washington, D.C.

[21] Appl. No.: 501,638

[22] Filed: Mar. 28, 1990

[51] Int. Cl.$^5$ ............................................. A01C 1/00
[52] U.S. Cl. .......................... 47/58; 800/DIG. 61; 47/DIG. 6
[58] Field of Search ........... 47/58; 800/200, DIG. 59, 800/61

[56] References Cited

U.S. PATENT DOCUMENTS 4,570,379 2/1986 Oglevee et al. ...................... 47/58
5,058,318 10/1991 Tammen .................................. 47/58

OTHER PUBLICATIONS

Thompson et al., (1957), *Vegetable Crops*, Fifth Edition, McGraw-Hill, N.Y., pp. 347-371.
Hartmann et al., (1968), *Plant Propagation*, 2nd Edition, Prentice-Hall, N.J., pp. 506-519.
Stimart et al., (1981), Developmental Response of *Lilium longiflorum* Bulblets to Constant or Alternating Temperatures in vitro, J. Amer. Soc. Hort. Sci., 106(4), pp. 450-454.
Anderson, (1977), Rapid Propagation of Lilium, c.v. Red Carpet, in vitro, Annual Meetings in vitro, 13(3), p. 145.
Laurie et al., (1969), *Commercial Flower Forcing*, 7th Ed., McGraw-Hill, pp. 414-418.

*Primary Examiner*—Elizabeth C. Weimar
*Assistant Examiner*—Gary Benzion
*Attorney, Agent, or Firm*—M. Howard Silverstein; John D. Fado; Janelle S. Graeter

[57] ABSTRACT

A new and innovative technique of producing *Lilium elegans* Asiatic hybrid lily is disclosed. Very small bulbils from leaf axils of *L. elegans* receives sequential low-high-low temperature treatment before planting in the soil medium. After planting, scale leaves emerge and bulb weight increases. After about 13 scale leaves have emerged from the bulbs, the temperature is lowered to favor shoot emergence, preferably under long day photoperiod to accelerate shoot emergence and to induce flower bud formation. A desirable plant producing up to three flowers on a long stem is produced in about 270-300 days after harvesting bulbils, thus bypassing the field production phase of the bulb that lasts more than a year in the field.

5 Claims, 9 Drawing Sheets

METHOD FOR PRODUCING LILIUM ELEGANS

BACKGROUND OF THE INVENTION

1. Field of the Invention

The present invention relates to products and methods for the production of lily plants specifically *Lilium elegans* Thunb., from bulbils produced in leaf axils and *Lilium longiflorum* Thunb., lilies produced from seedlings or bulblets derived from tissue culture or leaf cuttings.

2. Description of the Prior Art

Conventional forcing of the Easter lily (*Lilium longiflorum*) requires treating the lily bulb for 42 days at 40°–45° F. to accelerate flowering, however, this conventional bulb cold treatment has the disadvantage of reducing the number of flower buds (Roh and Wilkins, Thesis Collection, Vol. 10, 1976, pp. 295–305, Yeungnam University, Daegu, Korea).

To increase the number of flower buds without delaying flowering time, 3 weeks of cold treatment at 40°–45° F. was followed by 1 to 3 weeks of 60° F. treatment period. This was again followed by an additional 3 weeks of cold treatment to give a total of 6 weeks of cold treatment (Roh and Wilkins, J. Amer. Soc. Hort. Sci., Vol. 102, 1977, pp. 235–242).

*L. lancifolium* required forcing of a sequential low temperature (45° F.) treatment for 20 days followed by high temperature (81° F.) for 7 days, and finally followed by low temperature for 20 days given to 330–430 mg bulbils produced 22 percent flowering plants in less than 7 months from bulbil harvest (Roh, S. M., J. Kor. Soc. Hort. Sci., Vol. 22, 1981, pp. 199–208).

Ultimately, bulb production can take up to two years. During this bulb production phase, there is a serious risk of disease and insect infestation that subsequently lowers bulb and plant quality. Currently, lily viruses pose a major threat to the production of a high quality crop.

Virus Information

Currently, lily viruses pose a major threat to the production of a high quality crop. Lily symptomless virus (LSV) is a virus that causes stunting and vegetative growth may be reduced by as much as 25 to 50 percent. The virus is transmitted by the melon aphid, *Aphis gossypii*. Infection is common and probably uniform in many *L. longiflorum* and Asiatic hybrid lilies.

Cucumber mosaic virus (CMV) causes a severe disease in lily when combined with LSV in *L. longiflorum*. This disease, known as fleck, produced foliar necrosis and death of the leaves. CMV is transmitted by the green peach aphid, *Myzus persicae* and mechanically by sap. A third virus infecting lily is tulip breaking virus. This virus causes a streak mottle symptom in lily leaves. Many small, irregularly shaped, light green flecks occur along the veins. Disease plants show premature death of the lower foliage. Tulip breaking virus is also transmitted by *M. persicae* and by sap. A fourth virus, lily virus X, is an important virus in Europe, but has not yet been identified in the U.S.

Additionally, several soilborne fungal diseases caused by *Fusarium oxysporum*, *F. solani*, *Cylindrocarpon radicicola*, *Rhizoctonia solani*, *Pythium spp.*, *Phytopthora spp.*, *Colletrotrichum lilii* and *Sclerotium rolfsii* could be more effectively controlled by eliminating the two year cycle of in-ground bulb production in the field that is normally a part of lily production. Therefore it can be seen that there is a need for methods that reduce the attendant disadvantages of the present prior art methods for lily production.

SUMMARY OF THE INVENTION

The cultural procedures described in this invention include production of plants from stem bulbils or from bulblets after tissue culture in a protected environment. Bulbils, bulblets, or seedlings are treated in the same manner as described in the summary of the invention. However, details will be explored based on bulbils as major propagules. It is possible to protect the lily plants from virus infection using this cultural method by reducing the chance of exposure to insects compared to bulb production in the field. When lily culture is initiated with pathogen-free stock, this new growing method allows production of a lily crop that is essentially free of the viruses described as lily symptomless virus, cucumber mosaic virus, tulip breaking virus and lily virus X.

The following methods were formulated so that high quality plants could be produced within a year in the greenhouse, bypassing bulb production phase in the field, starting from small and naturally forming bulbils of *L. elegans* hybrid lilies, particularly in 'Beni no Mai' and other new hybrids ('Yellow Blazer×Horner's Back Gold', 'Inferno'×'Beni no Mai' and 'Connecticut Lemonglow'×'Beni no Mai') which will be named Diamond Mountain series.

Bulbils harvested from leaf axils receive sequential low-high-low temperature treatments before potting in the growing medium. Following the initial development of scale leaves, the plants are grown under high light intensity, long photoperiod, and high temperature environments that are similar to the requirements of flowering of various Lilium species.

The scientific background that leads to this invention is based on the research results of the *Lilium longiflorum* Thunb., commonly known as Easter lily and of the *Lilium lancifolium* Thunb., commonly known as tiger lily.

It is an object of this invention to grow lilies that can produce 2 to 4 flowers on a strong stem longer than 60 cm within 300 days from the time of bulbil harvest, thus eliminating the traditional bulb production phase in the field presently lasting up to two years. Initially, the bulbil is the basic and starting propagules that requires selection of *Lilium elegans* hybrid lily cultivars.

One of the differences of this invention as compared to U.S. Pat. No. 4,570,379 is that propagation is performed without involving leaf cutting propagation. Most of *Lilium elegans* hybrid lilies cannot be propagated by leaf cuttings. Further, growth of bulbils while still attached on the leaf axil of the mother plant is accelerated under high light intensity and high temperature, conditions that prevail during summer months. When flowering of the mother stock plants occur around April and May, harvest of bulbils around June and July is possible.

Bulblets propagated by scaling of the 'Inferno', 'Sunray', and 'Connecticut Lemonglow' hybrid lilies were also tested. These three hybrid lilies do not naturally form bulbils. However, each of these three lilies failed to produce quality plants using similar methods described in the description of the preferred embodiment.

The method of growing *Lilium elegans* lily described in this invention is comprised of four parts:

a. Culture of disease-free mother stock plants to grow and flower around April-May in greenhouse environments., b. Harvesting of the bulbils from the mother stock plants that did not form scaly leaves;

c. A sequential low-high-low bulbil temperature treatment to break dormancy before potting and to induce an early scaly leaf formation after potting the temperature treated bulbils; and d. Providing optimum temperature, light intensity, and photoperiod treatment alone or in combinations during various growth and development stages until flowering., and e. Storing bulbs at proper development stages at 28° to 30° F. for up to 1 year before forcing in the greenhouse.

BRIEF DESCRIPTION OF THE DRAWINGS

FIG. 7 257 days after bulbil harvest, and after long day treatment, 15 scales (two outermost scales were dried) are formed and 37 true leaves longer than 1 mm in length were formed. At this time, microscopically distinguishable flower bulbs are observed.

DESCRIPTION OF THE PREFERRED EMBODIMENT

Step A. Bulbil formation

Figure 1:
FIG. 1 Formation of bulbils in the axil of the leaves of *L. elegans*. 'Beni no mai' lily. Bulbils are formed after flowering. Depending on the size of the bulbs at planting in the previous year, up to 80 bulbils weighing about 500 mg can be harvested in 60 days after flowering.

*Lilium elegans*, 'Beni no Mai' and new hybrids, Diamond Mountain Series, that will be named later, plants produce bulbils when lilies are forced in the greenhouse (FIG. 1). However, when lilies are forced outdoors, bulbil formation is greatly inhibited. Bulbil formation is a very effective method compared to scale propagation, tissue culture (requirement of laboratory facility), or leaf propagation (low propagation rate) methods. Additionally, pests and insects are easily controlled when mother plants are grown in a greenhouse.

Plants flower around April-May, resulting bulbils can be harvested anytime in June-July or 45-60 days after flowering.

Step B. Bulbil harvest

Figure 2:
FIG. 2 Bulbils with premature formation of scaly leaves before harvest. These types of bulbils should be separated out. Scaly leaf formation is either caused by late harvest of the bulbils from the stock plants or due to a loss of bulbs resulting from bulb rot.

Approximately 45-60 days after flowering, 400 mg-500 mg bulbils can be harvested. Bulbils weight may be as high as 1.4 g, after 120 days following flowering. However, due to premature sprouting of the bulbils while still attached to the mother stock plant (FIG. 2), bulbils must be harvested after they are separated from the leaf axil by pushing bulbils slightly.

Step C. Cold treatment given to the bulbil before potting

Bulbils are packed in moist (40-80 percent moisture content) peat moss or other inert materials and the following sequential temperature treatments are given:
20 DAYS OF 40°-45° F.-7 TO 14 DAYS OF 50°-55° F.-20 DAYS OF 40°-45° F.

Step D. Planting cold treated bulbils in pots

Figure 3:
FIG. 3 Early stage of growth showing scaly leaves. Plants are grown in 3-inch pots, pot to pot spacing. Plants are preferably grown in 4-inch pots.

For potted plant production using dwarf hybrids, each bulbil should be planted in 4- or 5-inch pots with growing medium containing soil (3:4:4, soil:peat moss:perlite) or any medium that does not contain soil. It is important to use pot sizes larger than 3-inch (FIG. 3) since only a few plants produced 2 flowers when grown in 3-inch pots during the first 90-120 days after potting. For cut flower production, bulbils can be planted into trays, the size being up to 3'×5', or ground beds. Bulbils planted in trays can be stored frozen for forcing year-round.

Step E. Temperature control after potting

Temperature is maintained at about 80°-90° F. during the day and 70°-80° F. at night. During a two-year experimental period, temperatures were maintained at 80°-100° F. during the day and 70°-85° F. at night from July to October.

Figure 4:
FIG. 4 Short but wide scaly leaf is finally formed after regular scaly leaves are formed during a 4-month period after potting.

The high temperature requirement after potting lasts for at least 3 months or until no new scaly leaves are forming. Generally 13 to 15 scaly leaves are formed from each bulbil (FIG. 4). The completion of scaly leaves formation is when short but wide scaly leaves develop. The upright growing pattern of the scaly leaves changes, and the center of the plants appear more open. This indicates that shoot is formed from the basal plate.

Step F. Light intensity and nutrition requirement during growth period described in Step E.

When stock plants are grown in a greenhouse, full sunlight transmitted through the glass is desired. During May-September, light intensity can be reduced to 60% level. Additional lighting at 18 W/m$^2$ from HID-HPS lamps given for 2-3 months after potting did not increase the number of flower buds at flowering.

During the entire growing period, plants are fertilized with 200 ppm N from water soluble fertilizer once a week. Slow release fertilizer can be incorporated into a growing medium.

Step G. Low temperature and long-day photoperiod treatment

Figure 5:
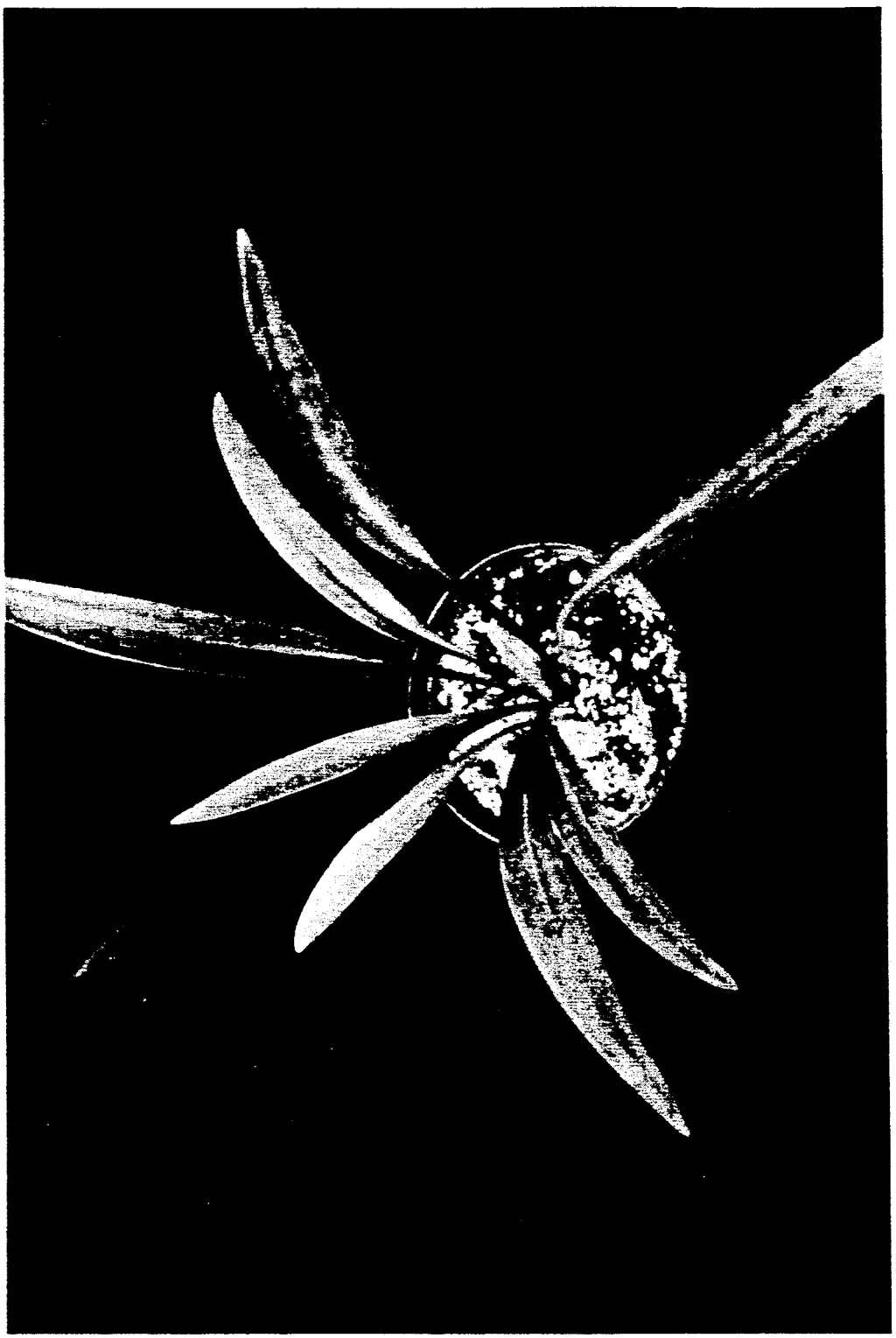
FIG. 5 After sequential low-high-low temperature treatments, bulbils are planted in 4-inch pots. Within 15 days, the first scaly leaf emerges and high light intensity lighting commences until scale leaves start to die naturally. About 13 to 15 scaly leaves are formed before showing the sign of the termination of scaly leaf formation.

When short and wide scaly leaves appear as the first sign of shoot formation (FIG. 5), night temperature is dropped to 50°-55° F., with day temperature maintained at 60°-70° F. The temperature duration should last until a few outer scaly leaves are easily broken from the base during watering or during spacing or moving pots. The ease with which the scaly leaves break may be a sign of the initiation of scaly leaf senescence, and also indicates that plants are being transformed from a bulbil stage, forming scaly leaves, to a bulb stage capable of stem elongation and receiving flowering stimulus treatment.

Figure 6:
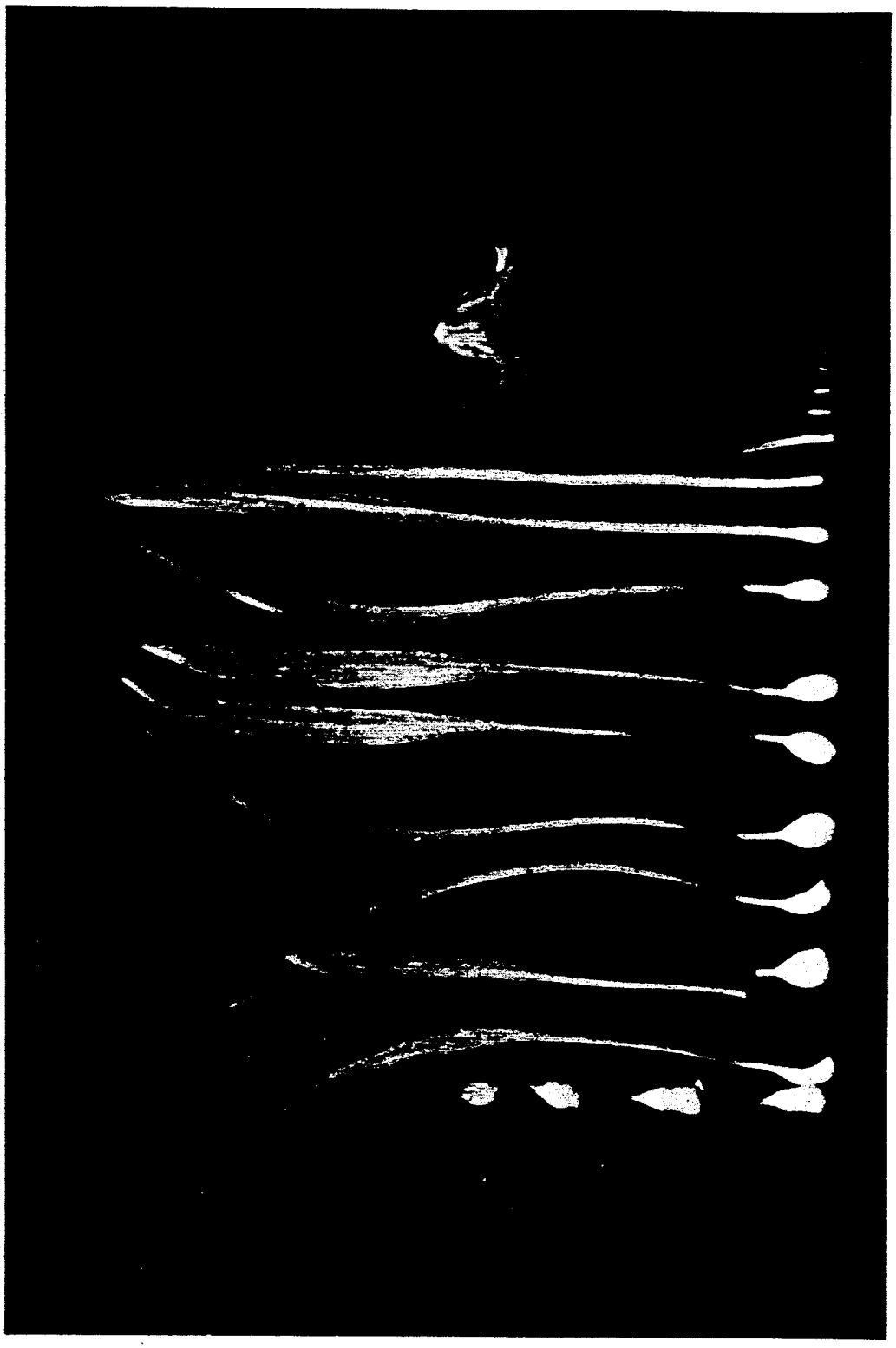
FIG. 6 Plant harvested 213 days after high light intensity treatment is shown. Four outermost scales do not form scaly leaves. A total of 13 to 15 scales or leaves longer than 0.5 mm in length is formed. The outermost scale leaf is easily broken off about 1 cm above the tip of the scale.

When scaly leaves start to separate easily from the bulbils, night temperatures should be maintained at 50°-55° F. for 40 to 60 days. During this time, long day treatment may additionally be given to stimulate shoot formation and subsequently flower bud initiation. Long day treatments are given by lighting from 4 p.m. to midnight or from 10 p.m. to 2 a.m. using incandescent light at the intensity of 1 or 2 W/m$^2$, respectively. After low temperature and long day photoperiod treatment, more than half of the scaly leaves may be separated from the plants (FIG. 6).

Step H.

After growing plants at 50°-55° for 40 to 60 days, whole tray or harvested bulbs can be stored at 28°-30° for up to one year for year-round forcing. Before and after freezing, bulbs are stored at 35°-40° for one week.

Step I. Transplanting

When bulbils are grown in 4-inch pots for pot plant production, they can be transplanted into 5-inch pots to increase the potential to produce up to 4 flowers. For cut flower production, plants can be grown in trays or ground bed.

Step J. Temperature manipulation after growth stages described in Step G

Figure 7:
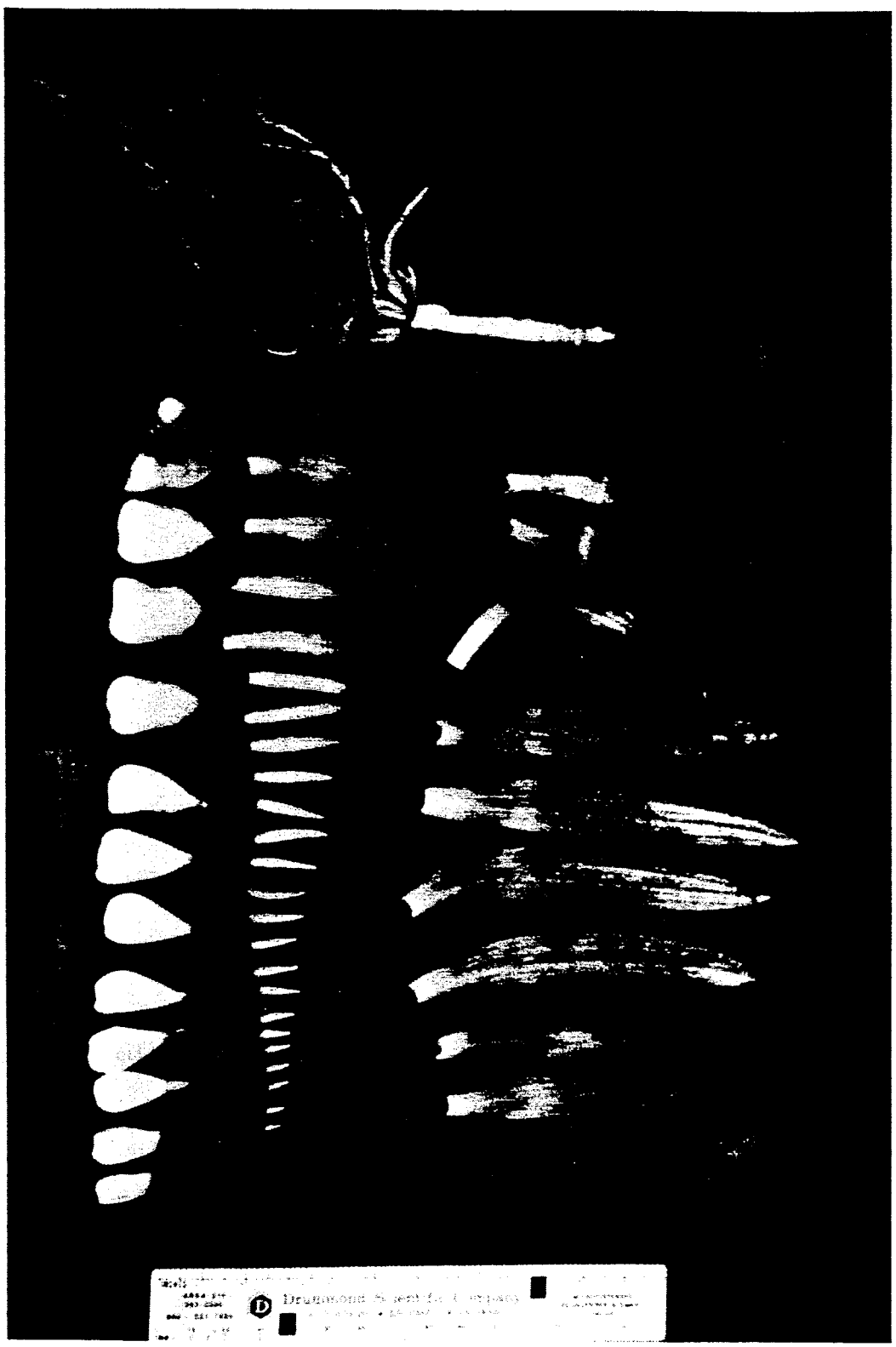
Figure 8:
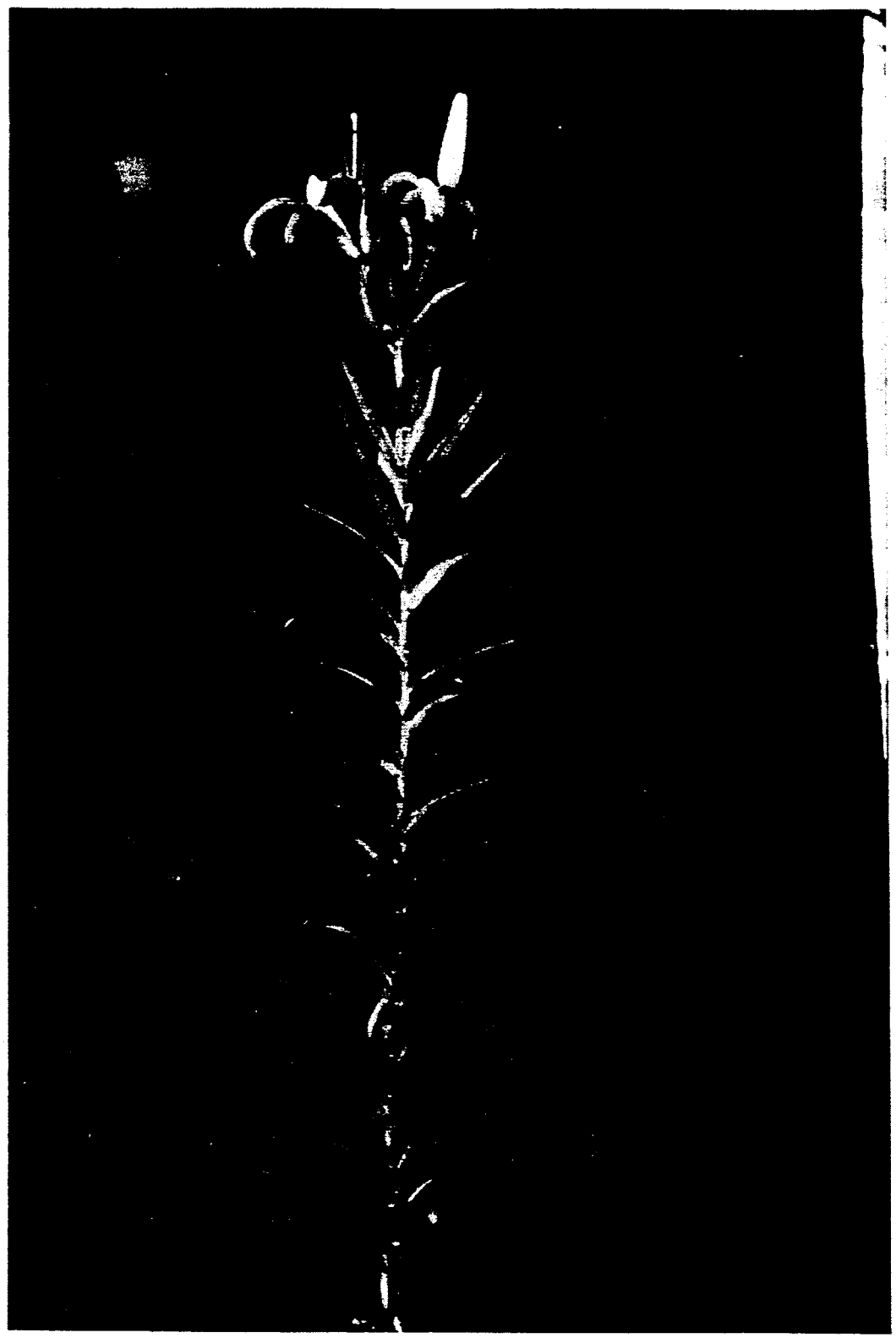
FIG. 8 Plant at flowering with a minimum of two to three flowers on a stem length longer than 60 cm is produced.
Figure 9:
FIG. 9 Plant at flowering in 4 inch pot with 4 flowers.

Temperature is raised to 70° F./60° F., day/night until flowering. Shoots will emerge within about 40-50 days at the above temperature and from shoot emergence to flowering, it will take about 100 days. Plants near the flower bud initiation (275 days after bulbil harvest) (FIG. 7) and at flowering (FIG. 8 and 9) are shown.

ALTERNATIVE EMBODIMENTS

Alternately, instead of using bulbils, bulblets as initial propagules are also obtained by tissue culture, leaf cuttings, and scaling or seeds, particularly in *L. longiflorum*. These propagation methods are very important using cultivars that do not produce bulbils naturally.

Tissue Culture. Bulbs stored for a minimum of 4 weeks at low temperatures ranging from 32° to 55° F. are used to obtain vernalized scales. Scales are separated from basal plate and cut into 2 to 5 mm long pieces. Scales are then incubated generally in tissue culture medium for Lilium species. During the culture period it is preferable to place the culture in the dark, keeping the temperature range from about 65° to about 80° F. Bulblets weighing about 400 mg can be harvested 50 days after tissue culture.

Leaf Cuttings. Not all cultivars can be propagated by leaf cuttings. However, several cultivars, i.e., 'Inferno' are propagated by leaf cutting. Also, most of the *Lilium longiflorum*, Easter lily cultivars are also propagated successfully. Leaves are stuck in an inert medium, e.g., vermiculite, perlite, or peat moss and propagated under mist. After 45 to 60 days, bulblets can then be harvested.

Scaling. Scales are separated and packed in moist inert medium composed of vermiculite, perlite, peat moss, sawdust or other inorganic packing materials. After placing bags at 65°-80° F. for 45 to 60 days, bulblets are separated.

Seeds. Germinated seeds of *L. longiflorum* are grown for 3 months until they form 3-4 leaves. Individual seedling is then transplanted into 4" pots. After obtaining bulblets with artificial propagation methods mentioned above, bulblets are treated at temperatures described by the previous method.

The cold treatment should be given as sequential low-high-low temperature treatment where low temperature is 40°-45° F. and high temperature is 50°-55° F. and the duration of low, high, low temperature treatments should last 20, 7 to 14, and 20 days, respectively.

The growing conditions of the bulbils immediately after planting requires high light intensity prevailing in the greenhouse during summer and temperatures should be maintained higher than 70° F. under a natural long day photoperiod.

Optimum temperatures to induce shoot emergence is 70°/50°-55° F., day/night, and long day photoperiod treatment is given either by lighting from 2200 to 0200 HR or from 1600 to 2400 HR from incandescent light sources for 40 to 60 days.

After induction of shoot emergence, optimum forcing temperature for growth and flower bud initiation and development means 70°/60° F., day/night, and this temperature is maintained until flowering.

I claim:

1. A method of growing Lilium species and hybrid lily cultivars, in Lilium species in which bulbil formation can be induced, said method comprising:
   a) culturing post-flowering mother stock lily plants capable of producing aerial bulbils and forcing said lily plants in a greenhouse for a period of about 45 to about 60 days after flowering;
   b) harvesting bulbils having a weight of about 500 mg from the leaf axils of said mother stock lily plants;
   c) treating the harvested bulbils to sequential temperatures changes of about 40°-45° F. for about 20 days then to about 50°-55° F. for about 7 to about 14 days followed by about 40°-45° F. for about 20 days;
   d) potting the treated bulbils in pots containing growing medium, trays, or ground beds;
   e) growing the potted bulbils at temperatures of about 80°-90° F. during the day and about 70°-80° F. during the night to promote scaly leaf formation and until termination of the scaly leaf formation;
   f) maintaining the bulbils at temperatures of about 60°-70° F. during the day and about 50°-55° F. during the night to induce shoot emergence; and
   g) growing said shoots to flower.

2. A method of growing Lilium species and hybrid lily cultivars, in Lilium species in which bulbil formation can be induced, said method comprising:
   a) harvesting aerial bulbils from post-flowering mother plants, wherein said bulbils have not formed scaly leaves while attached to said mother plants, and wherein said mother plants are of predetermined hybrid lily cultivars that form bulbils freely and do not initiate flower buds 10–30 days after completion of conventional bulb cold treatment;

b) treating the harvested bulbils to sequential temperature changes of about 40°–45° F. for about 20 days then to about 50°–55° F. for about 7 to about 14 days followed by about 40°–45° F. for about 20 days;

c) potting the treated bulbils in pots containing growing medium, trays, or ground beds;

d) growing the potted bulbils at high, about 80°–90° F., temperatures to promote scaly leaf formation and until termination of scaly leaf formation;

e) maintaining the bulbils at low, about 50°–55° F., temperatures to induce shoot emergence and until shoot formation occurs and flower buds are initiated; and f) forcing flowering at a temperature of about 60° F. during the day and about 70° F. during the night.

3. A method of growing hybrid lilies and Lilium species, in Lilium species in which bulbil formation can be induced, said method comprising:

a) harvesting aerial bulbils from post-flowering predetermined mother stock hybrid lily plants;

b) grading the harvested bulbils by weight and selecting bulbils that have not formed scaly leaves or presprouted while still attached to the leaf axils of the mother stock plants;

c) packing the graded and selected bulbils in a moistened growing medium;

d) treating the packed bulbils to sequential temperature changes of about 40°–45° F. for about 20 days then to about 50°–55° F. for about 7 to about 14 days followed by about 40°–45° F. for about 20 days;

e) growing the treated bulbils at high, about 80°–90° F., temperatures and sunlight conditions comprising either full sunlight or, from May through September, about 60% of full sunlight intensity, to promote scaly leaf formation and until termination of scaly leaf formation;

f) maintaining the bulbils at temperatures of about 60°–70° F. during the day and about 50°–55° F. during the night and under conditions of a long-day environment, said environment selected from the group consisting of lighting from about 1600 hours to about 2400 hours with incandescent light of about 1 W/m$^2$ and lighting from about 2200 hours to about 0200 hours with incandescent light of about 2 W/m$^2$, to induce shoot emergence and until such time as shoots emerge and flower buds are initiated;

g) growing plants at forcing temperatures sufficient for shoot elongation; and h) growing plants to flower.

4. A method of claim 2, wherein step d) additionally comprises a long day photoperiod.

5. The method of claim 3, wherein step f) additionally comprises transplanting into larger sized pots, when scaly leaves become easily separated.

* * * * *